United States Patent
Messerly et al.

(10) Patent No.: US 7,621,927 B2
(45) Date of Patent: Nov. 24, 2009

(54) MEDICAL INSTRUMENT WITH A MECHANICAL COUPLING

(75) Inventors: Jeffrey D. Messerly, Cincinnati, OH (US); Barry T Jamison, Fairfield, OH (US); Steven P. Smolik, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 239 days.

(21) Appl. No.: 11/091,224

(22) Filed: Mar. 28, 2005

(65) Prior Publication Data

US 2006/0217743 A1  Sep. 28, 2006

(51) Int. Cl.
*A61B 17/10* (2006.01)
(52) U.S. Cl. .................. 606/142; 606/139; 606/143; 606/205
(58) Field of Classification Search .................. 606/139
See application file for complete search history.

(56) References Cited

U.S. PATENT DOCUMENTS 5,666,965 A * 9/1997 Bales et al. ................. 600/562
6,210,398 B1 * 4/2001 Ouchi ............................ 606/1
2001/0047124 A1 * 11/2001 Yamamoto ................... 600/101
2002/0038119 A1   3/2002 Weber et al.
2003/0191478 A1 * 10/2003 Kortenbach et al. ......... 606/142
2004/0143163 A1 * 7/2004 Palmer et al. ................ 600/204

FOREIGN PATENT DOCUMENTS

| EP | 1607055 A |   | 12/2005 |
| GB | 1666797 A |   | 7/1921  |
| GB | 2258028 A | * | 1/1993  |

OTHER PUBLICATIONS

EPO Search Report dated Jul. 17, 2006 for corresponding patent application, European Patent Application No. 06251638.

* cited by examiner

*Primary Examiner*—(Jackie) Tan-Uyen T. Ho
*Assistant Examiner*—Melanie Tyson
(74) *Attorney, Agent, or Firm*—Gerry Gressel

(57) ABSTRACT

A medical instrument is disclosed having a flexible tube, an end effector, and an actuator. A control member, such as a control wire, can extend through the flexible tube. A mechanical coupling is disclosed for attaching the control member to the actuator. A method for mechanically coupling the control member to the actuator is also disclosed.

21 Claims, 6 Drawing Sheets

MEDICAL INSTRUMENT WITH A MECHANICAL COUPLING

FIELD OF THE INVENTION

The present invention relates to medical instruments, and more particularly, to instruments which may be used through flexible endoscopes.

This application cross references and incorporates by reference the following patent application: U.S. patent application Ser. No. 10/867,501 filed on Jun. 14, 2004, titled "Endoscopic Surgical Instrument Having a Force Limiting Actuator". This application cross-references the following application filed on even date herewith: U.S. patent application Ser. No. 11/091,168 "Mechanical Coupling Method".

BACKGROUND OF THE INVENTION

A physician may use a surgical clip applier to deploy a surgical clip that clamps a duct, vessel, or other tissue in the patient. Surgical clip appliers are particularly useful to control bleeding in regions of the body where restricted access to the surgical site may preclude suturing or stapling. A flexible clip applier, such as described in the above mentioned U.S. patent application Ser. No. 10/867,501 can be inserted through a working channel of a flexible endoscope, and can be used to perform procedures in the gastrointestinal tract of the patient. Such a flexible clip applier can employ a control member such as a steel wire for transferring mechanical force from a handheld actuator to a pair of end effectors coupled to the distal end of a flexible tube of the instrument. The operator may apply a significant force to the actuator, which may result in high mechanical stress in some of the small components of the instrument, especially at the mechanical coupling between the actuator and the control member. If this coupling should slip or break during usage, the instrument may become inoperable, resulting in the additional time, cost, and frustration of replacing the instrument during the medical procedure.

It can be desirable to ensure accurate assembly with respect to coupling a control member to an actuator because even a small assembly error may adversely affect the operation of the instrument. For example, incorrect positioning of the coupling may cause failure of the end effectors to sufficiently close or open. Manufacturers currently may use any one of a variety of methods for coupling the actuator to the control member. For example, in some instruments in which the control member is a steel wire, one or more bends are made in a portion of the wire, which is then sandwiched between interlocking members of a mechanical coupling, which is finally assembled into the actuator. This method has a disadvantage of needing to first create the bends in exactly the right location on the wire, and then to transfer the bent member into the interlocking members. In addition, wear of the forming dies used to create the wire bends, and spring back of the bent wire may also contribute to inaccurate assembly.

It can also be desirable to couple a control member to an actuator with a secure attachment without damage to the control member. Manufacturers sometimes use a method that incorporates a mechanical coupling assembled onto the wire and locked into place with a setscrew tightened against the wire. The security of such an attachment may depend on the setscrew tightness on the wire. Because of the necessarily small size of the mechanical coupling and setscrew, the holding force of the setscrew may not be sufficient to prevent slippage of the mechanical coupling on the wire for high forces. Also, to prevent damage to the wire that may be caused by tightening the setscrew, and to prevent stress-induced wire breakage during usage of the instrument, some manufacturers place a thin-walled metallic tube over the wire prior to insertion into the mechanical coupling, and the setscrew is tightened to crush the tube and pinch the wire. The tube also facilitates the coupling of two or more wires to an actuator.

In both of the methods just described, there may be process-related variation of holding force of the mechanical coupling on the wire. In addition, the cost of specially designed setscrews can become significant in high volume manufacture.

Applicants have recognized the desirability of an improved device and method for coupling a control member to an actuator, such as to reduce variation of holding force, minimize assembly error, reduce component costs, and/or minimize damage to the control member.

SUMMARY OF THE INVENTION

In one embodiment, the present invention provides a medical instrument. The medical instrument can include a flexible tube; an actuator associated with a proximal portion of the flexible tube; an end effector associated with a distal portion of the flexible tube; a control member extending through the flexible tube for transmitting force to the end effector upon actuation of the actuator; and a coupling receiving the control member and conveying a force to the control member upon actuation of the actuator. A portion of the control member, which can be a control wire, can be deformed in a first direction after being received within the coupling. The coupling can include a retaining member, which can be a non-threaded spring pin. The retaining member can be inserted in the receiver in a in a second direction different from the first direction. The retaining member can maintain the position of the control member with respect to the coupling, such as by maintaining the deformation of the control member within the receiver.

In one embodiment, the coupling can define a first passageway extending through the length of the coupling for receiving the control member; a second passageway for receiving the retaining member, wherein at least a portion of the second passageway intersects the first passageway; and a third passageway for providing tool access to deform the control member, wherein at least a portion of the third passageway intersects the first passageway. Prior to inserting the retaining member in the receiver, a tool can be inserted into the third passageway to deform the control member in a direction perpendicular to the first passageway. The third passageway can extend beyond the intersection of the third passageway and the first passageway a distance greater than or equal to a dimension of the control member.

A method for adapting a control member to receive loading in a medical device is also provided. In one embodiment, the method comprises the steps of providing a control member and a coupling. The coupling can comprise a receiver, the receiver having a first passageway extending in a first direction for receiving the control member; and a second passageway extending in a second direction, the second passageway at least partially intersecting the first passageway. The method further comprises the steps of inserting a portion of the control member into the first passageway of the receiver;

deforming a portion of the control member disposed within the receiver in a third direction different from the first and second directions; and inserting a retaining member in the second passageway after deforming the portion of the control member to maintain the position of the control member relative to the receiver.

DETAILED DESCRIPTION OF THE INVENTION

Figure 1:
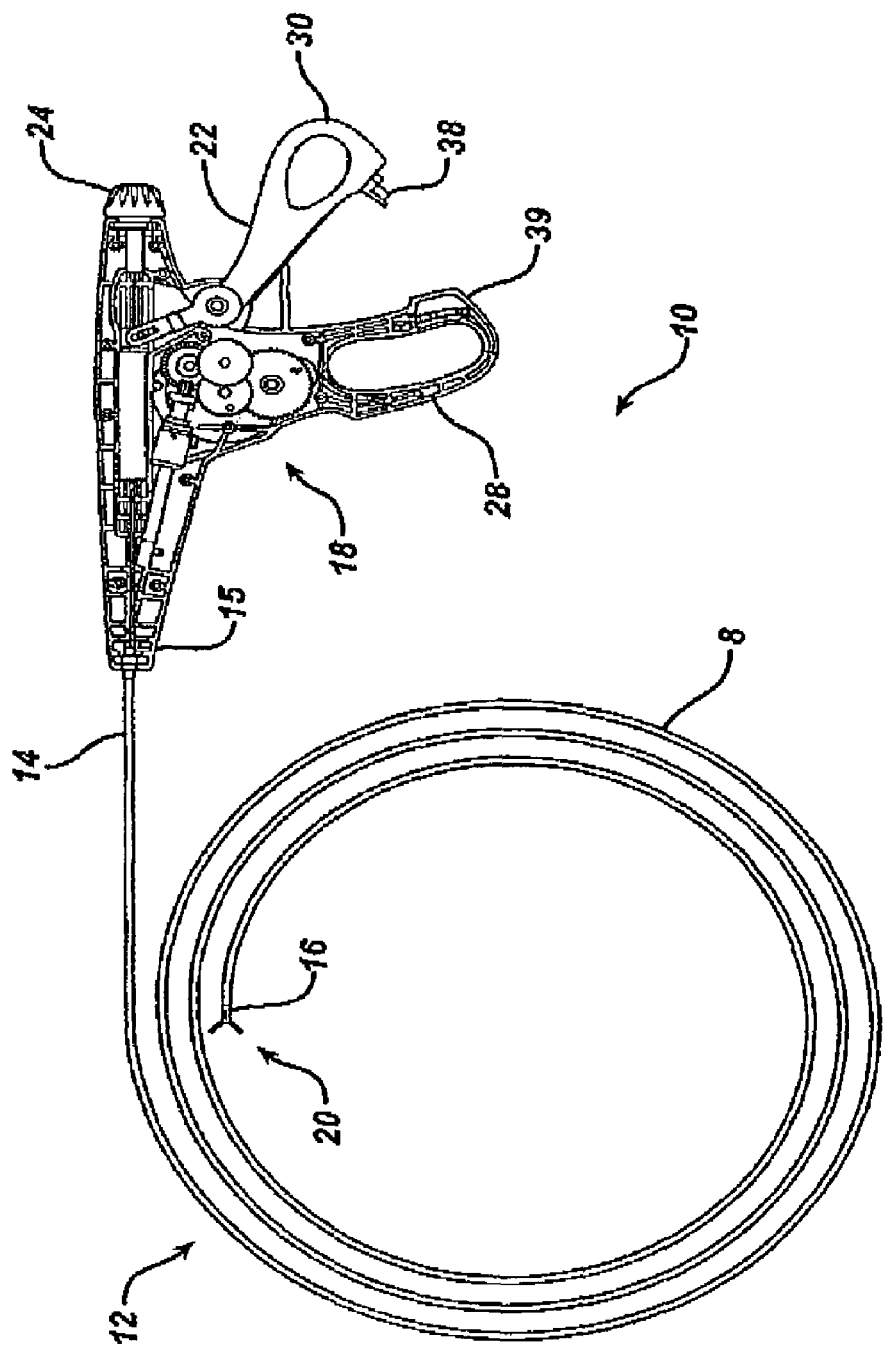
FIG. 1 is a side view of a flexible endoscopic instrument 10, including an actuator 18 that is shown without a left cover.

Referring now to the Figures, in which like numerals indicate like elements, FIG. 1 discloses a flexible, endoscopic instrument 10, also referred to as a medical instrument 10, having a flexible tube 12 with a distal end 16 and a proximal end 14. Proximal end 14 operably attaches to an actuator 18. In the embodiment shown, flexible endoscopic a instrument 10 is a clip applier, such as is described in the aforementioned U.S. patent application Ser. No. 10/867501. Flexible tube 12 can comprise a length of flat wire coil (which can be for example, about 3 mm in diameter by about one meter long) covered with a smooth, plastic outer sheath 8, as is known in the art for the manufacture of flexible, endoscopic instruments. A pair of end effectors 20 can be coupled to distal end 16 of flexible tube 12. End effectors 20 and flexible tube 12 can be small enough to easily slide through the access channel of a conventional, flexible endoscope from outside the patient to the tissue site inside of the patient.

Figure 2:
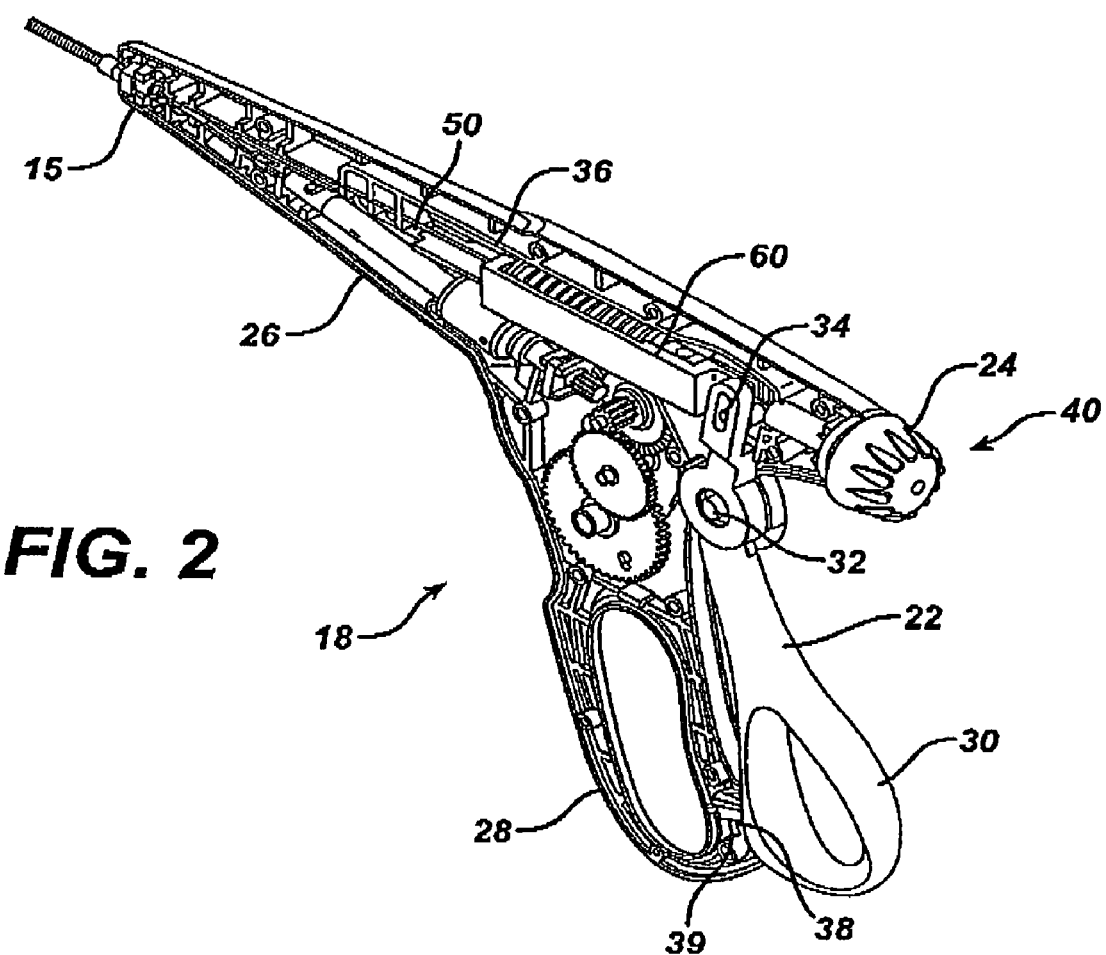
FIG. 2 is a perspective view of actuator 18 shown in FIG. 1, and showing a force limiting spring assembly 60.

Actuator 18, shown in FIG. 1 and FIG. 2, can include a frame 26 with a distal end 15 and a proximal end 40, a stationary grip 28, and a movable grip 30. In FIG. 1, movable grip 30 is shown in an open position, which for this embodiment corresponds to end effectors 20 being in an open position. In FIG. 2, movable grip 30 is shown in a closed configuration, which corresponds to end effectors 20 being in a closed configuration. A hook 38 can be positioned on movable grip 30 to detachably lock into a latch 39 positioned on stationary grip 28. Engagement of hook 38 with latch 39 can hold movable grip 30 in the closed position. Movable grip 30 can include a lever 22 pivotally attached to frame 26 by a lever pivot 32.

Actuator 18 can include a force limiting spring assembly 60 that is slidably retained in a track 36 of frame 26. A member associated with the spring assembly 60 (such as a pin 34 disposed at or near the proximal end of the assembly 60 and which can extend into and engage a surface of slot formed in a clevis of the lever 22) can be employed to transfer force from lever 22 to spring assembly 60, such that spring assembly 60 moves in the proximal direction in track 36 when an operator moves movable grip 30 from the open position in FIG. 1 to the closed position shown in FIG. 2, and such that spring assembly 60 moves in the distal direction when an operator moves movable grip 30 from the closed position to the open position.

A control member for transmitting forces from the actuator 18 to the end effectors 20 can be in the form of a wire 50. Wire 50 can extend through flexible tube 12. Wire 50 can have a distal portion which is operatively associated with end effectors 20, and a proximal portion operatively associated with assembly 60. Wire 50 can have a diameter of less than 0.1 inch, and in one embodiment can have a diameter of about 0.024 inches (approximately 0.6 mm) and can be formed of hardened steel. When spring assembly 60 translates in the distal direction, wire 50 translates in the distal direction an equal or smaller distance. When spring assembly 60 translates in the proximal direction, wire 50 translates in the proximal direction an equal or smaller distance. In the embodiment shown, a rotation knob 24 can be operatively associated with a proximal end of the wire 50 such that an operator may turn a rotation knob 24 in either direction (clockwise or counter clockwise) to cause wire 50 to rotate in a like direction, and thus causing end effectors 20 to rotate in a like direction.

Figure 3:
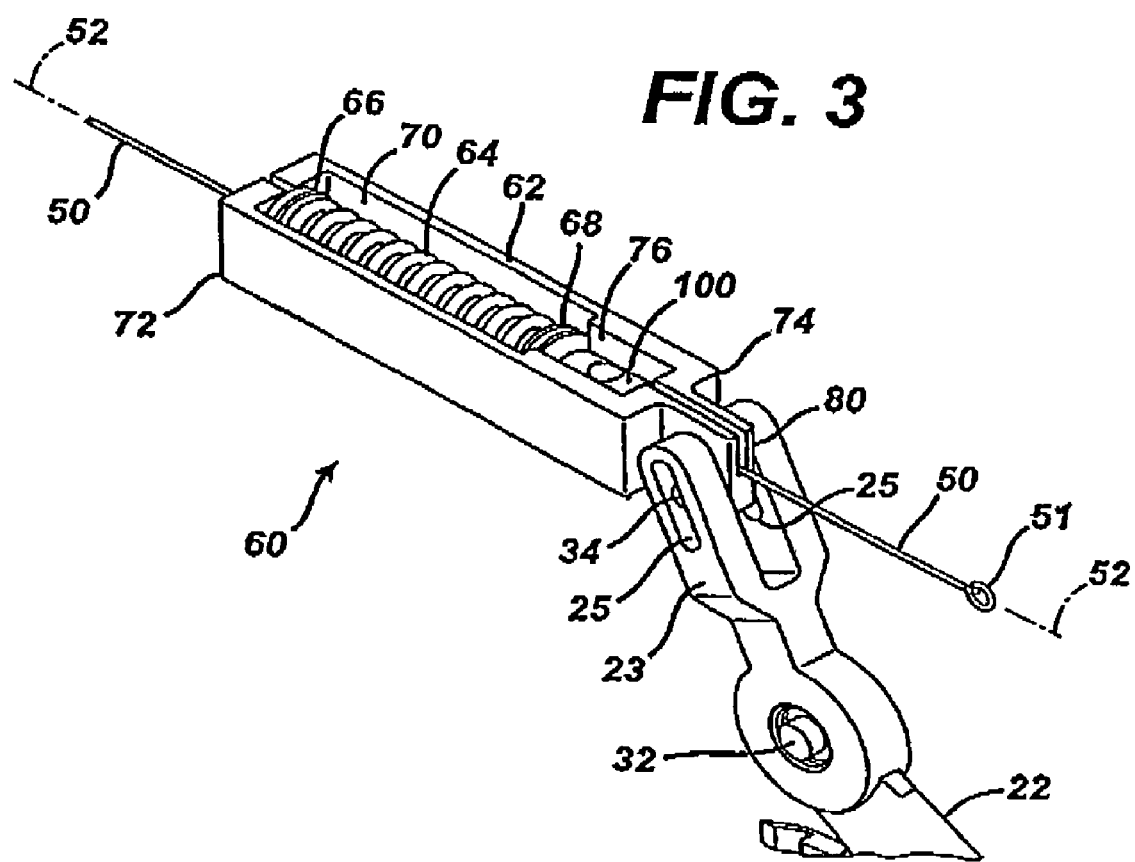
FIG. 3 is an enlarged view of force limiting spring assembly 60 shown in FIG. 2, showing a mechanical coupling 100.

FIG. 3 is an enlarged view of force limiting spring assembly 60, shown coupled to lever 22 of movable grip 30. As shown in FIG. 3, a clevis 23 extending from lever 22 can include slots 25 for receiving pin 34. In FIG. 3, a portion of wire 50 extends through spring assembly 60, to be disposed proximally of the assembly 60. Spring assembly 60 can include a spring 64, a mechanical coupling 100, a proximal end cap 68, a distal end cap 66, and a linkage or spring assembly frame 62.

Force limiting spring assembly 60 can be employed to limit the maximum tensile force imparted to wire 50 by closure of lever 22, and can assist in preventing accidental damage to end effectors 20 or excessive clamping force on tissue by limiting the maximum tension of wire 50. When the tensile load in wire 50 reaches a predetermined amount, further closure of lever 22 results in compression of spring 64 converting further movement of movable grip 30 into potential energy stored in spring 64. This may occur, for example, if the operator clamps end effectors 20 onto excessively thick or hard tissue. In addition, spring assembly 60 allows for variation of the required translation of wire 50 from the open configuration to the closed configuration, and vice versa. The required translation of wire 50 to open and close end effectors 20 may differ slightly when flexible tube 12 is relatively straight as compared to when flexible tube 12 is curved while positioned in the gastrointestinal tract of the patient. This is because bending of the wound wire coil in flexible tube 12 may cause a slight increase in the effective length of flexible tube 12 along its longitudinal axis, resulting in a small relative movement between wire 50 and flexible tube 12. Operation of spring assembly is more fully described in the above mentioned U.S. patent application Ser. No. 10/867,501.

Figure 4:
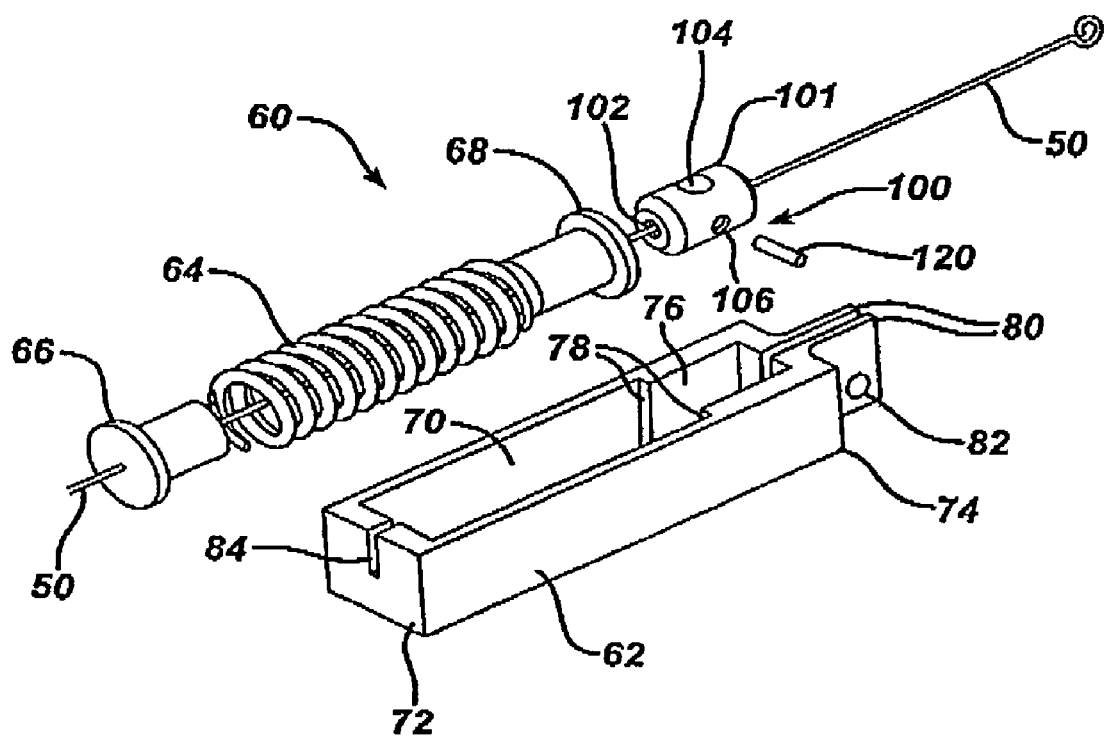
FIG. 4 is an exploded, perspective view of force limiting spring assembly 60 shown in FIG. 2 and FIG. 3.

Now referring to FIG. 3 and FIG. 4, spring assembly frame 62 can include a distal end 72, a proximal end 74, and a longitudinal axis 52 extending there between. Spring assembly frame 62 can have an elongated box shape and a smooth finish. Spring assembly frame 62 may be made from any one of a number of rigid materials, including a metal such as stainless steel or an aluminum alloy, or an injection molded polymer such as a polycarbonate or polyetherimide. Spring assembly frame 62 can include a spring enclosure 70 for retaining spring 64, and a mechanical coupling enclosure 76 for retaining mechanical coupling 100. Proximal end 74 of spring assembly frame 62 can include a pair of projections in the form of fins 80 projecting proximally from frame 62. Fins 80 can include holes 82 for receiving pin 34 there through. Distal end cap 66 can receive the distal end of spring 64 and abut against the inside of distal end 72 of spring assembly frame 62. Proximal end cap 68 can receive the proximal end of spring 64 and can bear against a portion of frame 62 (such as a surface of ledge 78 of spring enclosure 70) when movable grip 30 is in the open position.

Spring 64 may be loosely retained or partially compressed in spring enclosure 70, depending on the initial force desired for operating movable grip 30 from the open position. Spring 64 can be a conventional compression spring preferably made of a corrosion resistant metal such as stainless steel. The spring rate of spring 64 may vary depending on the requirements of the specific medical application of medical instrument 10. When movable grip 30 is in the closed position, and flexible tube 12 is curved due to insertion into the gastrointestinal tract of a patient as previously described, for example, spring 64 can be selected to provide a longitudinal force that is approximately equal to the maximum tensile force desired for wire 50.

Wire 50 passes through a slot 84 in distal end 72 of spring frame 62 and passes through spring frame assembly 60 approximately coaxially with longitudinal axis 52. Wire 50 slides freely through distal end cap 66, spring 64, and proximal end cap 68 during operation. Mechanical coupling 100 comprises a receiver 101 and a retaining member, which can be in the form of pin 120. Mechanical coupling 100 can be secured to wire 50 and can abut proximal end cap 68. When an operator actuates movable grip 30 from the open position to the closed position, longitudinal force of spring 64 bears against mechanical coupling 100, thus increasing tension of wire 50. Wire 50 extends proximally between fins 80 of spring frame 62 to a distal end 51 which can be formed for attachment to rotation knob 24.

Figure 5:
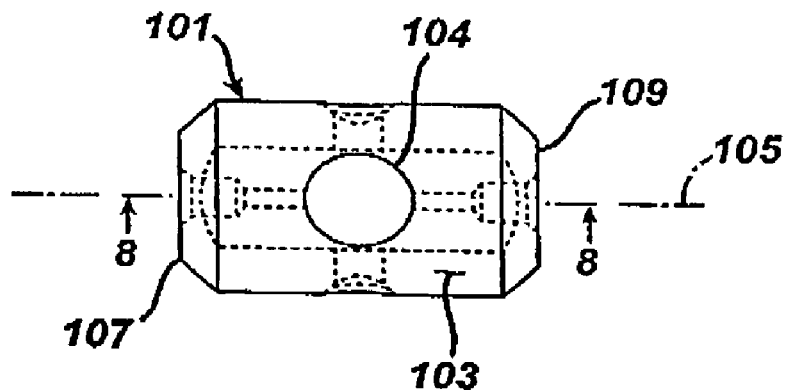
FIG. 5 is a top view of a receiver 101 of mechanical coupling 100 shown in FIG. 3.
Figure 6:
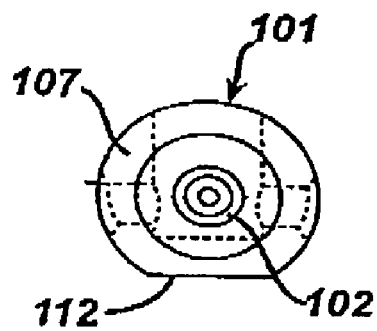
FIG. 6 is an end view of receiver 101 shown in FIG. 5.
Figure 7:
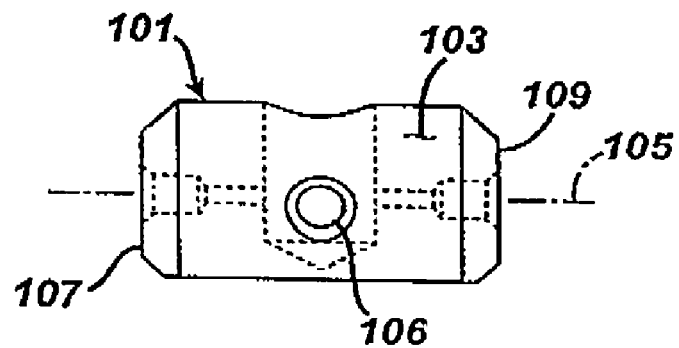
FIG. 7 is a side view of receiver 101 shown in FIG. 5.

FIG. 5 is a top view, FIG. 6 is an end view, and FIG. 7 is a side view of receiver 101, of mechanical coupling 100. Receiver 101 can be made of a relatively rigid material, such as a metal. Suitable metals include but are not limited to brass, aluminum, or stainless steel. Receiver 101 may also be made of a high strength plastic such as 40% glass filled nylon. In the embodiment shown, receiver 101 is a circular cylinder having a first end 107, and second end 109, and a first passageway, such as wire hole 102 extending through receiver 101 from first end 107 to second end 109 along a longitudinal axis 105. In the embodiment shown, the portions of wire hole 102 near first end 107 and second end 109 have a larger diameter than the portion of wire hole 102 in the middle portion of receiver 101 to facilitate manufacture and assembly of mechanical coupling 100.

Receiver 101 can have a smooth, exterior surface 103, so that receiver 101 may freely translate and rotate about the longitudinal axis of spring assembly 60 (see FIG. 4.) Wire hole 102 can be sized such that the diameter of the portion of the wire hole 102 in the middle portion of the receiver 101 is slightly larger than the diameter of wire 50, thus allowing a close sliding fit for assembly onto wire 50.

Figure 9:
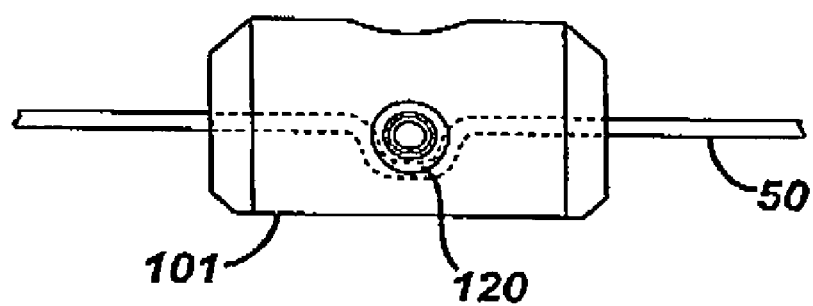
FIG. 9 is a side view of mechanical coupling 100 assembled onto wire 50.

Receiver 101 can also include a second passageway, such as pinhole 106 located approximately midway along the length of receiver 101. Pinhole 106 can extend from an outer surface 103 of receiver 101 and be substantially perpendicular to axis 105. Pinhole 106 can be positioned to be in intersecting relationship to wire hole 102. Pinhole 106 may extend entirely through receiver 101, as shown in this embodiment, or be a blind hole, and extend only partially through receiver 101. The diameter of pinhole 102 can be sized to provide a tight fit for pin 120 (FIG. 9), and may have a nominal diameter, for example, of about 1.5 mm. Pin 120 may have any suitable configuration, such as, bu not limited to, that of a steel roll pin, a spring pin (which provides radially outward biasing of pin 120 against the inner surface of hole 102), a solid steel pin, a straight knurled steel pin, a helical knurled steel pin, a knurled steel pin, a hex steel pin, or a tapered steel pin.

Figure 8:
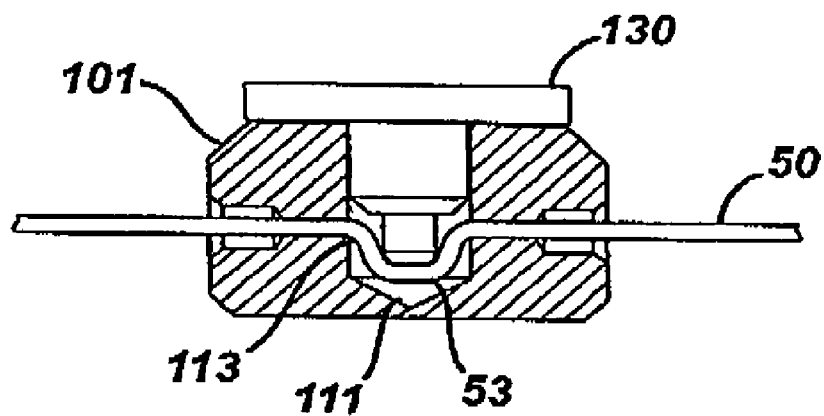
FIG. 8 is a cross-sectional view of receiver 101 shown in FIG. 5 at line 8-8, shown with a tool 130 deforming a wire 50 passing through receiver 101.

As shown in FIG. 5, receiver 101 can further comprise a third passageway, such as tool hole 104 located approximately midway along the length of receiver 101. Tool hole 104 can be substantially perpendicular to longitudinal axis 105, and substantially perpendicular to pinhole 106. Tool hole 104 can have a diameter that is sized to provide a close sliding fit for a tool 130 shown in FIG. 8. Tool hole 104 may extend entirely through receiver 101, or be a blind hole as shown in FIGS. 7 and 8, extending only partially through receiver 101. Wire hole 102, tool hole 104, and pinhole 106 can be substantially perpendicular to each other, and can be in intersecting relationship with one another. The longitudinal axes of the holes 102, 104 and 106 may intersect, but may also be offset from each other.

FIG. 8 shows receiver 101 during one step of a method for assembling mechanical coupling 100 to wire 50. Tool 130 may be a steel punch, for example, that is mounted on an arbor press or held by hand and used with a hammer or the like. When wire 50 is positioned at the desired location in wire hole 102, tool 130 is advanced inwardly in hole 104 to deform wire 50. For instance, tool 130 can be forcefully inserted into tool hole 104 with press, thus deforming wire 50 and resulting in a wire deformation 53. Alternatively, tool hole 104 could be formed with internal threads and tool 130 could be in the form of a threaded screw, such that the tool 130 could be threaded into hole 104 to deform wire 50.

Tool hole 104 may extend into receiver 101 only as deep as required to create wire deformation 53 so that pin 120 may be pressed into pinhole 106 immediately after tool 130 is removed from tool hole 104. In one embodiment, the tool hole 104 extends beyond the intersection of tool hole 104 and wire hole 102 a distance greater than or equal to the diameter of wire 50 and the diameter of wire hole 102, so that the deformed portion of wire 50 is displaced a distance greater than or equal to the diameter of the wire 50, and greater than or equal to the diameter of wire hole 102. If desired, tool 130 could include a through hole for receiving pin 120, such that once pin 120 is pressed into pinhole 106 to pass through the hole in tool 130, the tool 130 would be retained in the receiver 101 by pin 120.

Once pressed into pinhole 106, pin 120 maintains wire deformation 53 and maintains the receiver at a desired location along the length of wire 50, thus locking receiver 101 onto wire 50. Tool hole bottom 111 may have a drill point shape, a hemispherical shape, a flat shape, or another shape. In one embodiment, wire 50 is made of hardened spring steel, and receiver 101 is made of a softer material such as brass, so that an interface 113 between wire 50 and receiver 101, located at the intersection of wire hole 102 and tool hole 104, deforms to help seat wire 50 in receiver 101. A flat 112 on external surface 103 serves to help stabilize receiver 101 on a work surface while tool 130 is forcefully inserted into tool hole 104 during assembly of wire 50 to receiver 101.

A method for assembling mechanical coupling 100 onto wire 50 can include the following steps. The assembler inserts wire 50 through wire hole 102 of receiver 101 and determines a desired longitudinal location of receiver 101 on wire 50. Determining the desired longitudinal location of receiver 101 on wire 50 may be accomplished, for example, by positioning first end 107 of receiver 101 a predetermined distance from proximal end 14 of flexible tube 12 while end effectors 20 are in a closed position. The assembler then inserts tool 130 into tool hole 104 to create wire deformation 53. The assembler next removes tool 130 from tool hole 104, and immediately presses pin 120 into pinhole 106 of receiver 101 so that pin 120 maintains the deformed configuration of the wire 50, thus preventing wire deformation 53 from straightening when tension is applied to wire 50. For the spring assembly 60 shown in FIG. 4, distal end cap 66, spring 64, and proximal end cap 68 may first be captured onto wire 50 prior to assembling mechanical coupling onto wire 50 to form a subassembly that may then be positioned into spring assembly frame 62, and finally assembled into actuator 18.

Wire deformation 53 interlocks with pin 120 such that mechanical coupling 100 may transfer a longitudinal force (tensile or compressive) or a torsional force from actuator 18 to wire 50. In the embodiment shown in FIG. 1, end effectors 20 require a tensile force in wire 50 to close onto tissue, a compressive force to open, and a torsional force in either direction to rotate in a like direction. For applications in which mechanical coupling 100 transfers a longitudinal force to wire 50, exterior surface 103 of receiver 101 may act as a sliding bearing surface that interfaces with enclosure 76 of spring assembly frame 62. For applications in which mechanical coupling 100 transfers a torsional force to wire 50, exterior surface 103 may act as a rotating bearing surface that interfaces with enclosure 76 and proximal end cap 68 of force limiting assembly 60.

In the above method for assembling mechanical coupling 100 onto wire 50, a fixture may be provided that constrains receiver 101 and wire 50 in a desired position during assembly. Although the present invention has been described for use with a single metallic wire, those skilled in the art will appreciate that mechanical coupling 100 may similarly be assembled onto two or more wires. One or more of the wires may be sleeved with a short length of tubing. For instance, two or more wires may be enclosed within a short length of tubing, and the length of tubing (together with the wires inside the tubing) can be positioned in the receiver and deformed with the tool 130. Further, while the control member is shown as a control wire 50, other suitable control members can be in the form of a strip, tube, rod, cable, or cord that is made of any one or more combinations of various materials including metals, polymers, and natural or synthetic fibers.

While the present invention has been illustrated by description of a flexible, endoscopic clip applier, it is not the intention of the applicant to restrict or limit the spirit and scope of the appended claims to such detail. Numerous other variations, changes, and substitutions will occur to those skilled in the art without departing from the scope of the invention. The present invention has applicability to many other types of medical instruments, which comprise an actuator mechanically coupled to a control member for transferring a mechanical force. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended claims.

What is claimed:

1. A medical device comprising:
   a flexible tube;
   an actuator associated with a proximal portion of the flexible tube;
   at least one end effector associated with a distal portion of the flexible tube;
   at least one control member extending through the flexible tube for transmitting force to the end effector upon actuation of the actuator; and
   a coupling receiving the control member and conveying a force to the control member upon actuation of the actuator; wherein a portion of the control member is deformable along a first dimension after being received by the coupling, and wherein the coupling comprises a retaining member extending along a second dimension different from the first dimension to maintain the position of the control member with respect to the coupling;
   wherein the coupling defines a first passageway extending through a length of the coupling for receiving the control member, wherein the first passageway extends along a third dimension, wherein the third dimension is different from the first and second dimensions, wherein the coupling further defines a second passageway extending from an outer surface of the coupling for receiving the retaining member, wherein at least a portion of the second passageway intersects the first passageway, wherein the second passageway extends along the second dimension.

2. The device of claim 1 wherein the retaining member is a non-threaded member.

3. The device of claim 1 wherein at least a portion of the coupling is formed of a material having a hardness less than the hardness of the portion of the control member received in the coupling.

4. The device of claim 1 wherein at least a portion of the coupling is formed of a material having a hardness less than the hardness of the retaining member.

5. The device of claim 1 wherein the retaining member comprises a pin.

6. The device of claim 1 wherein the retaining member comprises a spring pin.

7. The device of claim 1 wherein the coupling defines a third passageway for providing tool access to deform the control member, wherein at least a portion of the third passageway intersects the first passageway.

8. The device of claim 1 wherein the first, second, and third dimensions are all substantially perpendicular relative to one another.

9. A medical device comprising:
   a flexible tube having a proximal end and a distal end;
   an end effector associated with the distal end of the flexible tube;
   an actuator associated with the proximal end of the flexible tube;
   at least one control member extending through the flexible tube and having a deformed portion proximal of the flexible tube;
   a coupling for receiving the control member and conveying a force to the control member upon actuation of the actuator; wherein the coupling comprises:
      a receiver having a first end, a second end, a longitudinal axis, and an exterior surface, the receiver defining:
         a control member passageway for receiving the control member, the control member passageway extending along the longitudinal axis from the first end to the second end;
         a second passageway, the second passageway extending from the exterior surface of the receiver and intersecting the control member passageway;
         a third passageway, the third passageway extending from the exterior surface of the receiver and intersecting the control member passageway, wherein the third passageway extends beyond the control member passageway a distance greater than or equal to a dimension of the control member, the third passageway providing access for deforming a portion of the control member disposed within the control member passageway, wherein the second passageway extends along a first dimension, wherein the third passageway extends along a second dimension different from the first dimension; and a retaining member insertable in the second passageway to maintain the deformed position of the control member relative to the receiver.

10. The device of claim 9 wherein the control member has a diameter, and wherein the third passageway extends beyond the control member passageway a distance greater than or equal to the diameter of the control member.

11. The device of claim 9 wherein the retaining member is non-threaded.

12. The device of claim 9 wherein the retaining member is biased radially outwardly to engage an inside surface of the second passageway.

13. The device of claim 9 wherein the receiver is operatively associated with a force limiting assembly for limiting the load carried by the control member.

14. A coupling assembly for transmitting a load to a control member, the coupling assembly comprising:

a frame;

a receiver supported with respect to the frame to rotate about a longitudinal axis and translate along the longitudinal axis, the receiver having a first end, a second end, and an exterior surface disposed between the first and second ends, the receiver further including a control member passageway extending from the first end to the second end through the length of the receiver along the longitudinal axis, a second passageway extending from the exterior surface of the receiver and intersecting the control member passageway, and a third passageway extending from the exterior surface of the receiver and intersecting the control member passageway;

a control member extending through the control member passageway such that a portion of the control member extends proximally from the receiver and a portion of the control member extends distally from the receiver, and wherein a portion of the control member disposed within the control member passageway is deformed in a direction generally parallel to a longitudinal axis of the third passageway;

a retaining member disposed in the second passageway to engage the deformed portion of the control member and maintain the position of the control member relative to the receiver.

15. The device of claim 14 wherein the third passageway extends beyond the intersection of the third passageway and the control member passageway.

16. The device of claim 14 wherein the third passageway extends beyond the control member passageway a distance greater than or equal to a dimension of the control member.

17. The device of claim 14 wherein the control member has a diameter, and wherein third passageway extends beyond the control member passageway a distance greater than or equal to the diameter of the control member.

18. The device of claim 14 wherein the retaining member is non-threaded.

19. The device of claim 14 wherein the retaining member is biased radially outwardly to engage an inside surface of the second passageway.

20. The device of claim 14 wherein the control member comprises at least one wire.

21. The device of claim 14 wherein the control member comprises at least one wire sleeved with a short length of tube.

* * * * *